United States Patent [19]

Engvall et al.

[11] 4,391,749
[45] Jul. 5, 1983

[54] METHOD FOR THE PURIFICATION OF COLLAGENS

[75] Inventors: Eva S. Engvall; Erkki I. Ruoslahti, both of Olivenhain, Calif.

[73] Assignee: La Jolla Cancer Research Foundation, La Jolla, Calif.

[21] Appl. No.: 313,326

[22] Filed: Oct. 19, 1981

[51] Int. Cl.$^3$ .................. A61K 35/16; C07G 7/00; C08H 1/06; C09H 1/00
[52] U.S. Cl. ........................... 260/123.7; 260/112 B
[58] Field of Search ........................ 260/112 B, 123.7

[56] References Cited

U.S. PATENT DOCUMENTS 4,104,266  8/1978  Wickerhauser ............... 260/112 B
4,210,580  7/1980  Amrani ........................ 260/112 B
4,341,764  7/1982  Wallace et al. ............. 260/112 B X

OTHER PUBLICATIONS

Engvall et al., Int. J. Cancer: 20, 1-5, (1977).
Ruoslahti et al., Biochimica et Biophysica Acta, 534 (1978), 210-218.
Ruoslahti et al., Coll. Res., vol. 1, (1981), 95-128.

Primary Examiner—Howard E. Schain
Attorney, Agent, or Firm—Hubbard & Stetina

[57] ABSTRACT

Collagen affinity matrices are prepared, useful for separating collagenous substances from other high molecular weight proteinaceous substances. Fibronectin is fragmentated chemically or by enzymatic digestion, etc. Fragments of fibronectin, which retain the collagen-binding site but are severed from other binding sites of intact fibronectin, are selected and coupled to solid support material.

10 Claims, No Drawings

METHOD FOR THE PURIFICATION OF COLLAGENS

The invention described herein was made in the course of work under a grant or award from the Department of Health and Human Services.

The present invention relates to chromatographic methods and materials for separating high molecular weight proteinaceous substances and more particularly to methods and materials for isolating collagenous substances from mixtures of high molecular weight proteinaceous substances.

BACKGROUND OF THE INVENTION

Collagen is a fibrous protein that occurs in vertabrates as a chief constituent of connective tissue. A number of different collagens have been derived from various sources, such as skin, bone, cartilage, etc. Collagens, in general, are insoluble in aqueous media; however, collagens are known to exist which are soluble. Other collagens may be solubilized by various methods including pH adjustment, heat treatment, reduction, etc. For example, Collagen I, the most common collagen found in the skin, occurs naturally in fibers made up of cross-linked triple-stranded helices. Removal of the cross-linked regions by pepsin treatment and/or unwinding of the strands by heating leads to greater solubility. Means of distinguishing solubilized fragments of insoluble collagens is of utility in the study of collagens.

Gelatin, a product obtained from prolonged heating of collagen-containing tissue, is known to bind with fibronectin, an extracellular matrix and blood glycoprotein, and it is known that fibronectin can be readily isolated by chromatography on an affinity matrix prepared by coupling gelatin to a solid phase (Engvall and Rusolahti, *Int. J. Cancer* (20 (1977), 1-5).) It would seem that soluble or solubilized collagens could be isolated by a reverse affinity chromatography procedure in which fibronectin is coupled to a solid support. Fibronectin, however, in addition to having sites which selectively bind with collagen, has sites with affinity for a number of other high molecular weight proteinaceous substances including glycosaminoglycans, fibrinogen, actin, and surface material of Staphylococci and certain other cells. Furthermore, it has been found that, when intact fibronectin is coupled to certain solid supports, the number of available collagen binding sites is apparently reduced.

SUMMARY OF THE INVENTION

An affinity matrix is prepared by coupling fibronectin fragments to a solid support resin. Fibronectin is fragmented by chemical or enzymatic digestion, e.g., with trypsin or chymotrypsin digestion, or other suitable means. Fragments of various size are separated, e.g., by gel filtration, and fibronectin fragments having molecular weights in the 30–200 kilodaltons (kd) range are coupled to a solid support material. The support-fibronectin fragment matrices are useful in isolating collagens from other high molecular weight proteinaceous substances and for separating collagens having different fibronectin affinities. In particular, fibronectin fragments having molecular weights of about 30, 45, and 200 kd have been found applicable for isolating and separating collagens.

DETAILED DESCRIPTION OF THE PREFERRED EMBODIMENT

Naturally occuring fibronectin is a dimer of two polypeptides of molecular weights in the range of 220 to 225 kd. Fibronectin is known to bind to a number of high molecular weight proteinaceous substances at several binding sites, and the order of the binding sites in fibronectin is known. The $NH_2$-terminal domain contains a binding site for Staphylococci and fibrin(ogen). The next domain has the collagen-binding site. This is followed by the cell-binding site and, in the COOH-terminal part, the heparin-binding site. The site for actin-binding is located close to the collagen-binding site but is separate from it.

Water soluble fragments of 200 kd or less have been attained from fibronectin, and the fragments obtained by various methods are severed from some of the particular fibronectin-binding sites. Depending on the various collagen isolation requirements, such as the purity of the collagenous substance sought to be obtained, various fragments in the 30–200 kd range are advantageously used to form affinity matrices according to the invention. In particular, collagen affinity matrices have been prepared from fibronectin fragments having molecular weight of about 30, 45 and 200 kd.

Fibronectin fragments in the 200 kd range are isolated from human plasma cryoprecipitate. Cryoprecipitate is exposed to gelatin-Sepharose, and the bound fibronectin fragments are eluted therefrom. The fibronectin fragments resulting from cryoprecipitation are separated according to size by gel filtration, e.g. on Sephacryl S-200 gel filtration. Gelatin-binding polypeptide chains in the 180–200 kd range are obtained.

30 kd fibronectin fragments are produced by tryptic digestion of fibronectin. Trypsin digestion, depending on the time of digestion, yields varying portions of gelatin-binding polypeptide fragments in the 30 and 70 kd range. These are separated from other fragments by affinity chromatography on gelatin-Sepharose. The 30 kd fragments are isolated from the 70 kd fragments by gel filtration on Sephacryl S-200.

45 kd fibronectin fragments are produced by chymotrypsin digestion of fibronectin isolated from fresh human plasma or from plasma cryoprecipitate. Digestion of fibronectin with alpha-chymotrypsin yields mainly 45 and 120 kd fragments. The gelatin-binding 45 kd fragments are isolated from the 120 kd fragments by affinity chromatography on gelatin-Sepharose.

Each group of the fragments having collagen-binding sites, i.e., 30, 45, and 200 kd fragments, are coupled to a solid support to provide collagen affinity matrices of varying specificity. The 200 kd fragments bind to heparin and mediate cell attachment in addition to binding collagen. For work in isolating collagenous protein from cell culture media, contamination with proteoglycans and glycosaminoglycans is of concern. Although collagen isloated using support material-coupled 200 kd fragments contains very low levels of amino sugars as determined by amino acid analysis, it is generally preferred to use affinity matrices formed from the 30 and 45 kd fragments which bind only to collagen. The 45 kd fraction is more efficiently produced than the 30 kd fractions because trypsin digestion does not quantitatively preserve the collagen binding site of fibronectin and the 45 kd fraction may be preferred in certain applications for this reason.

Affinity matrices, in accordance with the present invention, are prepared by coupling fibronectin fragments with solid support in a manner which leaves collagen-binding sites of the fragments exposed. Suitable support material includes, but is not limited to agarose, dextran, glass and polystyrene.

A preferred support is an agarose resin sold under the name Sepharose 4B-CL. The fragments of 30, 45 and 200 kd are coupled to Sepharose activated with CNBr, and the resulting affinity matrices are designated respectively as 30K-S, 45K-S and 200K-S. The gelatin binding capacity, as determined from the amount of gelatin bound from an excess of gelatin solution, 100 $\mu$g/ml in phosphate buffered saline (PBS), is as follows: 30K-S, 0.15; 45K-S, 0.21; 200K-S, 0.18, expressed as mg of collagen bound per mg of fragment coupled.

The matrices with coupled fibronectin fragments have excellent stability. All three matrices, i.e., 30K-S, 45K-S, and 200K-S, have been used between 20 and 30 times each without noticeable decrease in binding capacity. The stability of these matrices, in combination with their unique collagen specificity, particularly 45K-S and 30K-S, makes them highly suitable for chromatographic applications.

The prepared collagen affinity matrices bind with collagen and collagen derivatives at generally neutral pH's, i.e., between about 6 and about 8. The bound collagen may be eluted from the matrices at more acid pH's, e.g., below about 3-4. It can also be diluted with dissociating agents such as urea and with chaotropic agents such as KSCN. Collagenous material may thus be separated from other high molecular weight proteinaceous material by exposing solutions of mixed proteinaceous material to a matrix with affinity for collagen. Collagenous substances bind to the matrix, and extraneous proteinaceous material is washed away. The bound collagenaceous material is then eluted from the matrix with appropriate buffers. Collagens having different affinities for the support-coupled fibronectin fragments may be separated by chromatography on the collagen affinity matrices.

The invention will now be described in greater detail by way of specific examples.

EXAMPLE I

Fibronectin in the form of human plasma cryoprecipitate was obtained from Alpha Theurapeutics, Pasadena, California. CNBr-activated Sepharose 4B-CL and Sephacryl S-200 were obtained from Pharmacia Fine Chemicals.

Intact fibronectin and large collagen binding fragments of fibronectin, present in the plasma cryoprecipitate, were isolated by adsorption to and elution from gelatin-Sepharose (Engvall and Ruoslahti 1977). Fifty grams of wet cryoprecipitate containing 230 mg of protein and 23 mg of fibronectin per gram, were suspended in 1000 ml PBS pH 7.2 at room temperature and centrifuged at 5000 rpm for 30 min. The supernatant was incubated with 1000 ml gelatin-Sapharose with stirring for 30 min. The gelatin-Sepharose was washed on a filter funnel with 10 L. PBS. Gelatin-Sepharose having bound collagen-binding substance was eluted with 4.5 M urea in 0.05 M Tris HCl, pH 7.0. The eluate was dialyzed extensively against deionized water. The precipitate formed during dialysis was removed by centrifugation, and the supernantant was lyophilized.

Fifty grams of cryoprecipitate was suspended in 1000 ml buffer, and 10 mg of either trypsin (Sigma type XI, DPCC treated) or chymotrypsin (Sigma type VII, TLCK treated) was added. The buffer used was 0.05 M Tris HCl, of pH 8.0 for trypsin and pH 7.0 for chymotrypsin. Incubation was carried out at 37° C. for 45 minutes. The enzymatic reactions were stopped by adding phenylmethyl sulfonyl flouride (PMSF) to 0.1 mM and egg white trypsin inhibitor to 100 $\mu$g/ml. After centrifugation, collagen binding fragments were isolated as above.

Gel filtration of fibronectin fragments was done on 100 cm columns of diameter 2.5 cm, packed with Sephacryl S-200 eluted with PBS; 200, 30 and 45 kd fragments respectively were obtained from undigested, trypsin-digested and chymotrypsin-digested fibronectin cryoprecipitate.

Protein fractions of the 200, 30 and 45 kd size were each dissolved in 0.1 M NaHCO$_3$; 0.5 M NaCl and were added to the CNBr-activated Sepharose at a ratio of 10-20 mg protein per ml Sepharose. 90-95% of the protein was coupled under these conditions.

EXAMPLE II

Culture medium from PF-HR 9 mouse endothelial cells was frozen and rapidly thawed. The pH was adjusted to 7.0, and the medium was clarified by centrifugation at 10,000 rpm for 15 min. One to two liters of medium were first passed through a 2.5$\times$10 cm column of gelatin-Sepharose to remove fibronectin and then through a 1.5$\times$10 cm column of 45K-S (fibronectin fragment-Sepharose). The latter column was washed with PBS containing 0.1 mM PMFS and eluted with 0.5 M acetic acid. All operations were done at 10° C. or lower.

A homogeneous collagenous protein having a single sub-unit of 160-190 kd was obtained from the eluent of a column of 45K-S prepared in Example I. Antisera prepared to this collagen specifically stained basement membranes in mouse tissues, and the isolated collagen resembles previously characterized basement membrane collagens (Type IV) with respect to size and compositional features of its constituent chains. However, unlike previously-described basement membrane collagens, this collagen does not appear to contain interchain disulfide cross links and may represent a hitherto undescribed form of basement membrane collagen.

This example illustrates the ability of collagen affinity matrices, prepared by coupling fibronectin fragments with a solid support, to selectively bind collagenous material. It further illustrates the potential such affinity matrices have for isolating particular types of collagens.

EXAMPLE III

The affinities of collagen type I and denatured collagen, i.e., gelatin, to 45K-S, prepared in Example I, were compared. Gelatin binds readily to 45K-S at 4° C. and at 37° C. Native collagen type I however, showed no demonstrable binding at 4° C. and only partial binding at 37° C. The differential affinity of different collagens to fibronectin support matrices demonstrates the usefulness of the collagen affinity matrices for chromatographic separation of different collagens.

While the invention has been described in terms of certain preferred embodiments, modifications obvious to one with ordinary skill in the art may be made without departing from the scope of the invention. For example, the 30, 45 and 200 kd fragments used in forming the affinity matrices represent fibronectin fragments having collagen-binding sites obtained by isolation from trypsin and chymotrypsin digests or from plasma cryoprecipitate, respectively, and it is obvious to one with ordinary skill in the art that fragments having other lengths may be obtained by other fragmentation procedures. Similarily, fibronectin obtained from alternative sources may yield fragments of different sizes. Matrices formed with fragments of other lengths are within the scope of this invention.

Various features of the invention are set forth in the following claims.

What is claimed is:

1. Affinity matrix material for separating collagen from other high molecular weight proteinaceous substances comprising:

solid chromatographic support material; and
    at least one fragment of fibronectin which retains thereupon collagen binding sites, said fragment having been severed from other binding sites of intact fibronectin, said fragment being coupled with said solid chromatographic support material leaving collagen binding sites thereof exposed to selectively bind collagenous material when used chromatographically without binding interfering high molecular weight non-collagenous proteinaceous substances.

2. The affinity matrix material of claim 1 wherein at least one of said fragments has a molecular weight of about 30 kd characterized as having the collagen specificity of such molecular weight fragment resulting from digestion of fibronectin with trypsin.

3. The affinity matrix material of claim 1 wherein at least one of said fragments has a molecular weight of about 45 kd characterized as having collagen specificity of such molecular weight fragment resulting from digestion of fibronectin with chymotrypsin.

4. The affinity matrix material of claim 1 wherein at least one of said fragments consists essentially of the sites of fibronectin which bind collagen, said fragment not including the sites of fibronectin which bind other high molecular weight proteinaceous substances.

5. The affinity matrix material of claim 1, 2, 3 or 4 wherein the solid chromatographic support material is Sepharose.

6. The affinity matrix material of claim 1, 2, 3 or 4 wherein the solid chromatographic support material is agarose, dextran, cellulose, polystyrene or glass.

7. In the chromatographic method for separating proteinaceous substances from one another, in which a mixture of such substances is passed by way of a solution over a chromatographic material, the improvement comprising separating collagen from other proteinaceous sustances by passing the proteinaceous material containing solution over an affinity matrix material comprising:

solid chromatographic support material; and
    at least one fragment of fibronectin which retains thereupon collagen binding sites, said fragment having been severed from other binding sites of intact fibronectin, said fragment being coupled with said solid chromatographic support material leaving callogen binding sites thereof exposed to selectively bind collagenous material when used chromatographically without binding interfering high molecular weight non-collagenous proteinaceous substances.

8. The chromatographic method of claim 7 wherein at least one of said fragments has a molecular weight of about 30 kd characterized as having the collagen specificity of such molecular weight fragment resulting from digestion of fibronectin with trypsin.

9. The chromatographic method of claim 7 wherein at least one of said fragments has a molecular weight of about 45 kd characterized as having collagen specificity of such molecular weight fragment resulting from digestion of fibronectin with chymotrypsin.

10. The chromatographic method of claim 7 wherein at least one of said fragments consists essentially of the sites of fibronectin which bind collagen, said fragment not including the sites of fibronectin which bind other high molecular weight proteinaceous substances.

* * * * *